(12) United States Patent
Kinoshita et al.

(10) Patent No.: US 8,580,056 B2
(45) Date of Patent: Nov. 12, 2013

(54) METHOD OF MAKING WEARING ARTICLE

(75) Inventors: Akiyoshi Kinoshita, Kagawa (JP); Natsuko Aoyagi, Kagawa (JP); Kayoko Tanaka, Kagawa (JP); Yasuhiko Kenmochi, Kagawa (JP)

(73) Assignee: Unicharm Corporation, Ehime (JP)

( * ) Notice: Subject to any disclaimer, the term of this patent is extended or adjusted under 35 U.S.C. 154(b) by 83 days.

(21) Appl. No.: 13/054,235

(22) PCT Filed: Jun. 30, 2009

(86) PCT No.: PCT/JP2009/061953
§ 371 (c)(1),
(2), (4) Date: Jan. 14, 2011

(87) PCT Pub. No.: WO2010/007880
PCT Pub. Date: Jan. 21, 2010

(65) Prior Publication Data
US 2011/0114248 A1  May 19, 2011

(30) Foreign Application Priority Data

Jul. 16, 2008  (JP) ................................ 2008-185326

(51) Int. Cl.
*A41H 37/00*  (2006.01)

(52) U.S. Cl.
USPC ............................................. 156/66; 156/91

(58) Field of Classification Search
USPC ............................................................ 156/66
See application file for complete search history.

(56) References Cited

U.S. PATENT DOCUMENTS

| | | | | |
|---|---|---|---|---|
| 5,851,205 A | * | 12/1998 | Hisada et al. | 604/390 |
| 6,447,497 B1 | * | 9/2002 | Olson | 604/389 |
| 8,282,616 B2 | * | 10/2012 | Lehto et al. | 604/385.3 |
| 2002/0099353 A1 | * | 7/2002 | Olson | 604/389 |
| 2005/0113793 A1 | | 5/2005 | Bianco | |
| 2008/0009816 A1 | | 1/2008 | Kenmochi et al. | |
| 2008/0249493 A1 | | 10/2008 | Kobayashi et al. | |

FOREIGN PATENT DOCUMENTS

| | | | | |
|---|---|---|---|---|
| JP | 2006-087568 | | 4/2006 | |
| JP | 2006-150068 | * | 6/2006 | ............. A61F 13/49 |
| JP | 2006-175007 | | 7/2006 | |
| JP | 2008-012115 | | 1/2008 | |

OTHER PUBLICATIONS

International Search Report from corresponding PCT application No. PCT/JP2009/061953 filed Oct. 6, 2009, 4 pgs.
European Supplementary Search Report from corresponding European application No. 09797808.4 filed May 2, 2013, 6 pgs.

* cited by examiner

Primary Examiner — Christopher Schatz
Assistant Examiner — John Blades
(74) Attorney, Agent, or Firm — Brinks Gilson & Lione

(57) ABSTRACT

A wearing article configured so that loop elements engaged with associated hook elements will not ride up or curl up in the course of the production process. Mount members are attached to an inner sheet in a front waist region so as to extend along first lateral zones of the front waist region and hook elements are attached to a chassis by the intermediary of these mount members. Loop elements are attached to the inner sheet in a rear waist region so as to extend along second lateral zones of the rear waist region. Third regions of the respective mount members are formed with sticking zones operatively associated with outer lateral edges of the respective loop elements. The sticking zones formed on the respective mount members are temporarily joined to the loop elements as the hook elements are engaged with the associated loop elements.

15 Claims, 5 Drawing Sheets

METHOD OF MAKING WEARING ARTICLE

RELATED APPLICATION

This application is a 35 U.S.C. §371 national phase filing of International Patent Application No. PCT/JP2009/061953, filed Jun. 30, 2009, through which and to which priority is claimed under 35 U.S.C. §119 to Japanese Patent Application No. 2008-185326, filed Jul. 16, 2008.

TECHNICAL FIELD

The present invention relates to a method of making wearing articles such as disposable diapers, toilet-training pants, incontinence briefs, menstruation panties or diaper covers.

RELATED ART

Conventionally, disposable diapers having front and rear waist regions detachably fastened along respective lateral zones thereof are known, for example, from the disclosure of PATENT DOCUMENT 1. According to this PATENT DOCUMENT 1, the diaper comprises a chassis having front and rear waist regions, a crotch region, a side facing a wearer's skin and a side facing a wearer's garment, and hook and loop elements respectively formed on the front and rear waist regions along the lateral zones thereof. The hook elements are attached to the lateral zones by intermediary of mount members. Such diaper is made from a web assembly in which each pair of the adjacent diapers having lateral zones being contiguous to each other fed in a machine direction in a process for making them.
[PATENT DOCUMENT 1] JP 2008-12115 A

DISCLOSURE OF THE INVENTION

Problem to be Solved by the Invention

In the process of making the diaper, the hook elements and the loop elements are fed in form of a mutually engaged assembly. To assure a desired engagement even if the hook elements and the loop elements are more or less displaced from the proper relative position, one of the areas occupied by the hook elements and the loop elements is dimensioned to be larger than the other. The hook elements have stiffness higher than that of the loop elements and therefore the area occupied by the loop elements is preferably dimensioned to be larger than the area occupied by the hook elements from the viewpoint of desirable flexibility of the diaper and undesirable irritation to the wearer's skin. However, dimensioning the area occupied by the loop elements to be relatively large necessarily a surplus area of the loop elements extending outward beyond the area of the hook elements and being free from engagement with the hook elements. Such surplus area free from engagement with the hook elements may sometimes ride up or curl up in the course of making the diaper and cause the hook elements to be disengaged from the loop elements and/or may deteriorate the productivity of the diaper.

In view of the problem as has been described above, an object of the present invention is to provide a method of making a wearing article improved so that loop elements engaged with the associated hook elements would not ride up or curl up in the course of production process.

Measure to Solve the Problem

According to the present invention, there is provided a method of making a wearing article comprising a chassis and a fastener assembly, the chassis having a longitudinal direction, a transverse direction, a side facing a wearer's skin and a side facing a wearer's garment, a first waist region corresponding to one of front and rear waist regions, a second waist region corresponding to the other of the front and rear waist regions and a crotch region extending between the first and second waist regions and the fastener assembly including first fastening regions provided along a pair of first lateral zones of the first waist region opposed to each other in the transverse direction and extending in the longitudinal direction and second fastening regions provided along a pair of second lateral zones of the second waist region opposed to each other in the transverse direction and extending in the longitudinal direction wherein the first fastening regions are detachably engaged with the second fastening regions and wherein the first fastening regions include hook elements and the second fastening regions include loop elements.

According to the present invention comprises the steps of forming the first fastening regions with sticking zones adapted to be temporarily joined to the second fastening regions, and bringing the hook elements of the first fastening regions into engagement with the loop elements of the second fastening regions and at the same time temporarily joining the first fastening regions to the second fastening regions by the sticking zones.

According to one embodiment, a process of making the wearing article includes a machine direction and a cross direction orthogonal to the machine direction and, in a course of continuously making the chassis, the transverse direction of the chassis corresponds to the machine direction and the method of making the wearing article further including the steps of feeding a web assembly forming the chassis in the machine direction and cutting the web assembly in the cross direction after the first fastening regions have been engaged with the second fastening regions.

According to another embodiment, each of the second fastening regions includes inner and outer side edges extending in the longitudinal direction and upper and lower ends extending in the transverse direction and the sticking zones are formed so as to face corners defined by the outer side edge and upper and lower ends of the second fastening regions in engagement with the first fastening regions.

According to still another embodiment, the first fastening regions include mount members extending outward beyond the first lateral zones by intermediary of which the hook elements are attached to the first lateral zones.

According to yet another embodiment, the sticking zones temporarily join the mount members to the loop elements.

According to further another embodiment, the loop elements occupy an area larger than an area occupied by the hook elements and the loop elements exposed outside the hook elements are temporarily joined to the mount members by the sticking zones.

Effect of the Invention

Temporary joint between the first fastening region and the second fastening region achieved by the sticking zones is effective to prevent the loop elements in the second fastening region from riding up or curling up from the first fastening region in the course of making the diaper. In consequence, precision and productivity of making the wearing article can be improved. In addition, the effect of such temporary joint by the sticking zones may be maintained in the course of putting the diaper on the wearer's body to restrict undesirable riding up or curling up of the loop elements during putting the diaper on the wearer's body. In consequence, the loop elements or the hook elements would not come in direct contact with the wearer's skin due to such riding up or curling up and cause any skin trouble.

The web assembly may be continuously fed and worked upon in the machine direction and cut in the cross direction after the first fastening region and the second fastening region have been brought in engagement. Such method effectively supports mass production of the wearing article.

The sticking zones are formed so as to face at least corners of the outer side edge and upper and lower ends of the second fastening regions in engagement with the first fastening regions. The sticking zones formed so as to face these corners at which the second fastening region is most apt to separate from the first fastening region are extremely effective to restrict riding up or curling up of the second fastening region.

The first fastening region includes the mount member which is sufficiently large to extend outward beyond the associated first lateral zone. In this way, the mount member can be prepared separately of the associated first lateral zone and appropriately selected depending on its particular purpose.

The sticking zones serve only for temporary joint between the mount members and the loop elements and thereby can temporarily join the first fastening region to the second fastening region without affecting the engagement between the hook elements and the loop elements.

The loop elements occupy an area larger than an area occupied by the hook elements and the loop elements exposed outside the hook elements are temporarily joined to the mount members by the sticking zones. In this way, the loop elements not in engagement with the hook elements can be temporarily joined to the first fastening region so as to restrict riding up or curling up of the loop elements in the course of making the wearing article.

Figure 1:
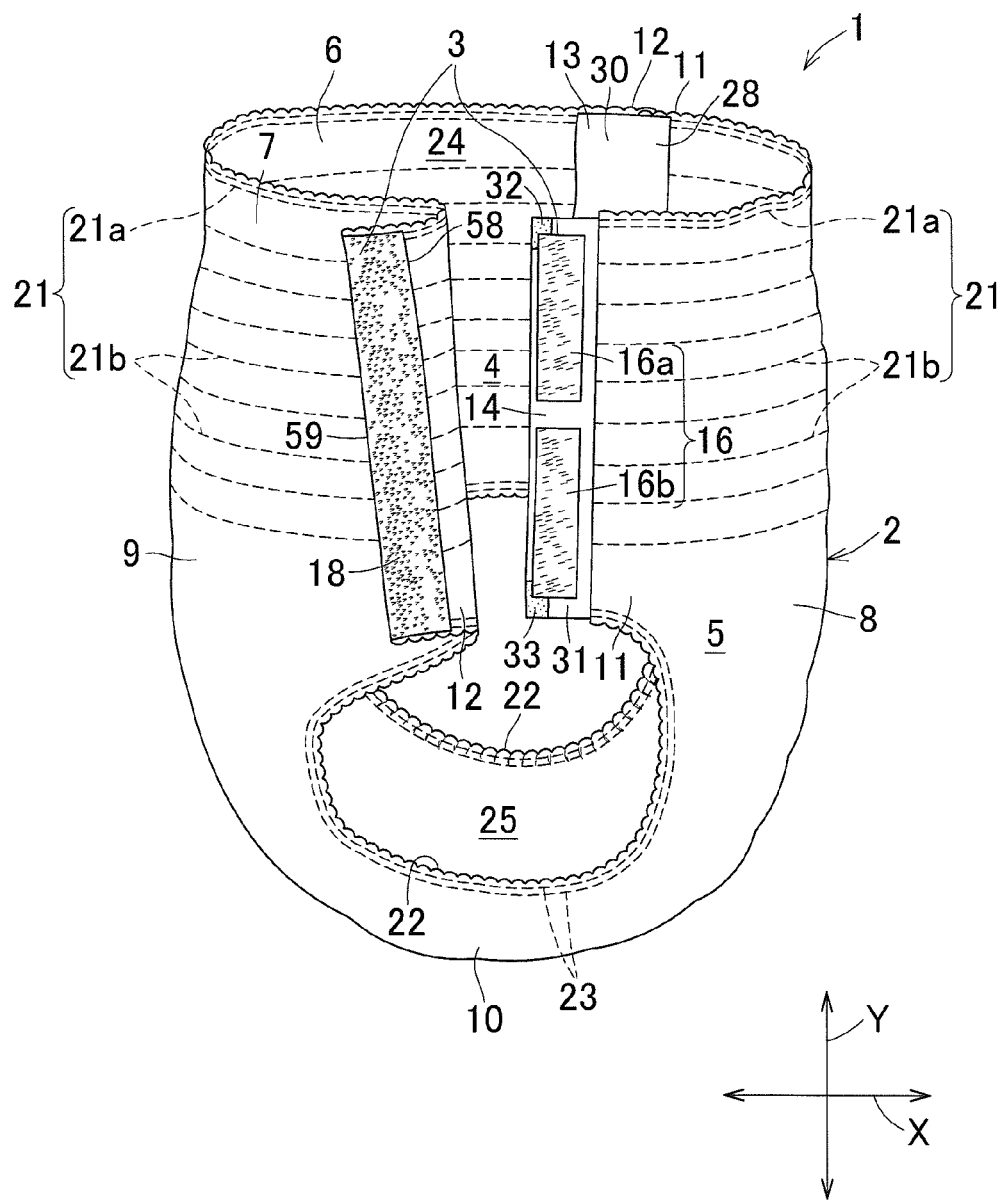
FIG. 1 is a perspective view of a diaper.

IDENTIFICATION OF REFERENCE NUMERALS USED IN THE DRAWINGS 1 diaper
2 chassis
3 mechanical fasteners
8 front waist region
9 rear waist region
10 crotch region
11 first lateral zones
12 second lateral zones
13, 14 mount members
15, 16 hook elements
17, 18 loop elements
26, 27 first regions
28, 29 second regions
30, 31 third regions
32, 33 first arrays of adhesion spots
35 first folding line
36 second folding line
41 first web
42 second web
44 cutting line
45 one end
46 opposite end
58 inner lateral edge
59 outer lateral edge
60 upper end
61 lower end

DETAILED DESCRIPTION OF THE PREFERRED EMBODIMENTS

Figure 2:
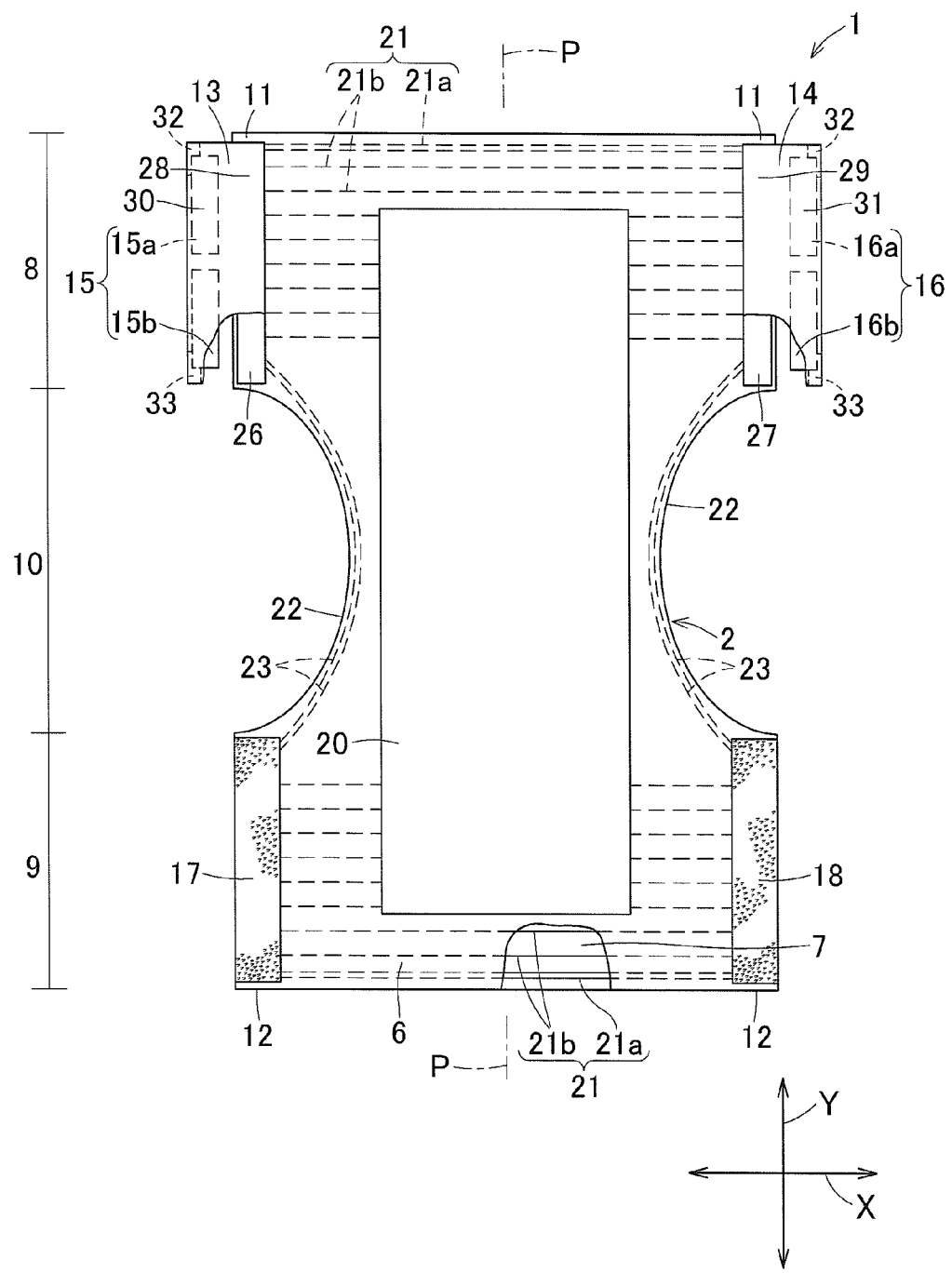
FIG. 2 is a plan view showing the diaper of FIG. 1 as has been flatly developed.

Details of the present invention will be more fully understood from the description made hereunder on an adult diaper as an exemplary embodiment with reference to FIGS. 1 through 5 of the accompanying drawings. FIG. 1 is a perspective view of the diaper 1 with one of transversely opposite lateral edges thereof being opened and FIG. 2 is a plan view showing the diaper 1 flatly developed as partially cut away for convenience of illustration. As illustrated, the diaper 1 comprises a liquid-absorbent chassis 2 and a mechanical fastener 3. The chassis 2 has a longitudinal direction Y, a transverse direction X, an inner side 4 facing the wearer's skin and an outer side 5 facing the wearer's garment. It should be appreciated that the nearside represents the inner side facing the wearer's skin and the remote side represents the outer side facing the wearer's garment with respect to a plane defined by FIG. 2. The chassis 2 comprises an inner sheet 6 defining the inner side 4 facing the wearer's skin, an outer sheet 7 defining the outer side 5 facing the wearer's garment, and a liquid-absorbent core 20 lying on the side of the inner sheet 6 directly facing the wearer's skin. The inner and outer sheets 6, 7 are formed of a liquid-pervious fibrous non-woven fabric or the like and the liquid-absorbent core 20 is typically formed of a mixture of fluff pulp fibers and super-absorbent polymer particles, all of these stock materials being conventionally used in the relevant technical field. Such chassis 2 includes a front waist region 8, a rear waist region 9 and a crotch region 10 extending between these front and rear waist regions 8, 9.

The front region 8 has a pair of first lateral zones 11 opposed to each other in the transverse direction X and extending in the longitudinal direction Y and the rear waist region 9 has a pair of second lateral zones 12 opposed to each other in the transverse direction X and extending in the longitudinal direction Y. The first lateral zones 11 respectively have a pair of elongate mount members (ear-like members) 13, 14 attached to the inner sheet 6 so as to extending in the longitudinal direction Y and a pair of hook elements 15, 16 constituting the mechanical fastener is attached to the chassis 2 by the intermediary of the mount members 13, 14. The first lateral zones 11, the mount members 13, 14 and the hook elements 15, 16 cooperated together to define first joining regions.

The mount members 13, 14 are formed, for example, of material such as a fibrous non-woven fabric and respectively comprise first regions 26, 27 boned to the inner sheet 6 along the respective first lateral zones 11, second regions 28, 29 folded back from the first regions 26, 27 onto the first regions 26, 27, and third regions 30, 31 extending outward from the second regions 28, 29 in the transverse direction X. The hook elements 15, 16 are bonded to the outer side facing the wearer's garment in the third regions 30, 31 of the mount members 13, extending outward. These hook elements 15, 16 are respectively divided in the longitudinal direction Y into upper halves 15a, 16a and lower halves 15b, 16b so as to be spaced from one another.

The inner sheet 6 has a pair of loop elements 17, 18 in the respective second lateral zones 12. The loop elements 17, 18 are dimensioned to have substantially the same length as a length of the second lateral zones 12 of the rear waist region 9 as measured in the longitudinal direction Y. In other words, these loop elements 17, 18 extend substantially along full length of the second lateral zones 12 in the longitudinal direction Y. The second lateral zones 12 cooperate with the loop elements 17, 18 to define second joining regions. The hook elements 15, 16 are detachably engaged with the associated loop elements 17, 18 wherein these loop elements 17, 18 are dimensioned to be larger than the hook elements 15, 16 in the longitudinal direction Y as well as in the transverse direction X. By dimensioning the loop elements 17, 18 to be larger than the hook elements 15, 16, it will be facilitated to engage these hook elements 15, 16 with the associated loop elements 17, 18 even if the hook elements 15, 16 are more or less misaligned with the associated loop elements 17, 18 in the longitudinal direction Y or in the transverse direction X. Thus no accurate alignment between the hook elements and the associated loop elements is required and correspondingly it becomes easy to put the diaper 1 on the wearer's body. As these hook elements 15, 16 and the loop elements 17, 18, the trademark "Velcro" or "Scotch Magic tape" commonly used in the relevant technical field may be used.

The front and rear waist regions 8, 9 are provided with waist elastic members 21 attached thereto under tension and contractibly so as to extend in the transverse direction. Specifically, these waist elastic members 21 comprise first elastic members 21a extending along a peripheral edge of a waist-opening 24 and second elastic members 21b between the first elastic members 21a and the crotch region 10. These waist elastic members 21 are sandwiched between the inner and outer sheets 6, 7 and bonded to at least one of the inner and outer sheets 6, 7. The waist elastic members 21 are formed of a plurality of strings, strands or tape-segments made of rubber wherein the second elastic members 21b are arranged substantially at regular intervals in the longitudinal direction Y so as to be attached to the front and rear waist regions 6, 7 substantially over entire areas of these two waist regions 6, 7 and thereby to elasticize the front and rear waist regions 6, 7 in the transverse direction X. By elasticizing the front and rear waist regions 6, 7, a desired fit of the front and rear waist regions 6, 7 to the wearer's body is assured not only to prevent leak of body fluids such as urine but also to improve the appearance of the diaper 1 put on the wearer's body.

The waist elastic members 21 in the front waist region 8 extend to respective inner sides of the mount members 13, 14 as viewed in the transverse direction X so that these elastic members 21 do not intersect with the respective mount members 13, 14. The hook elements 15, 16 are provided in third regions 30, 31 of the mount members 13, 14 extending outward from the second regions 28, 29 in the transverse direction X so that the waist elastic members 21 do not overlap the hook elements 15, 16. Also in the rear waist region 9, the waist elastic members 21 extend to the respective inner sides of the loop elements 17, 18 as viewed in the transverse direction X and do not overlap the loop elements 17, 18. Such arrangement that neither the hook elements 15, 16 nor the loop elements 17, 18 are overlapped by the waist elastic members 21 is effective to restrict the hook elements 15, 16 and the loop elements 17, 18 from getting wrinkled under contraction of the waist elastic members 21. Consequently, an area for engagement is prevented from being reduced due to getting wrinkles and thereby the engagement would not become unstable. Thus it is assured that the hook elements 15, 16 are firmly engaged with the associated loop elements 17, 18.

Between the first and second lateral zones 11, 12 in the longitudinal direction Y, peripheral edges 22 of respective leg-openings 25 are defined by opposite lateral edges of the crotch region 10 so as to be curved toward a longitudinal center line P-P bisecting a dimension of the diaper 1 in the transverse direction X. The diaper 1 is provided along the respective peripheral edges 22 with leg elastic members 23 contractibly attached thereto under tension. More specifically, these leg elastic members 23 are sandwiched between the inner and outer sheets 6, 7 and bonded or joined to at least one of these inner and outer sheets 6, 7. The leg elastic members 23 are formed of a plurality of strings, strands or tape-segments made of rubber so that contractile force of the rubber forming these elastic members 23 may bias the lateral edges 22 of the leg-openings 25 to fit about the wearer's thighs and thereby to prevent leakage of body fluids such as urine. The waist elastic members 21 as well as the leg elastic members 23 may be made of natural rubber or synthetic rubber such as polyurethane and, if this is convenient, these elastic members may be replaced by an elasticized non-woven fibrous fabric or an elastic plastic sheet, all of these stock materials for the elastic members being commonly used in the relevant technical field.

In the diaper 1 constructed as has been described above, the hook elements 15, 16 may be placed in engagement with the associated loop elements 17, 18 to join the front and rear waist regions 8, 9 to each other and thereupon to form the waist-opening 24 and a pair of the leg-openings 25. In this way, the diaper 1 is shaped into pull-on pants. To put such diaper 1 on the wearer's body, after the front and rear waist regions 8, 9 have been joined to each other, the wearer's legs may be inserted through the waist-opening 24 into the respective leg-openings 25 and then the diaper 1 may be pulled up along the wearer's waist. Alternatively, before the front and rear waist regions 8, 9 are joined together, the respective regions of the diaper 1 may be applied on the corresponding regions of the wearer's body and then the hook elements 15, 16 may be placed into engagement with the associated loop elements 17, 18 to join the front and rear waist regions 8, 9 so as to shape the diaper 1 in the pull-on pants. Thus the diaper 1 according to the present invention is convenient to put it on the wearer's body selectively in a pull-on pants fashion or an open-type diaper fashion.

Figure 3:
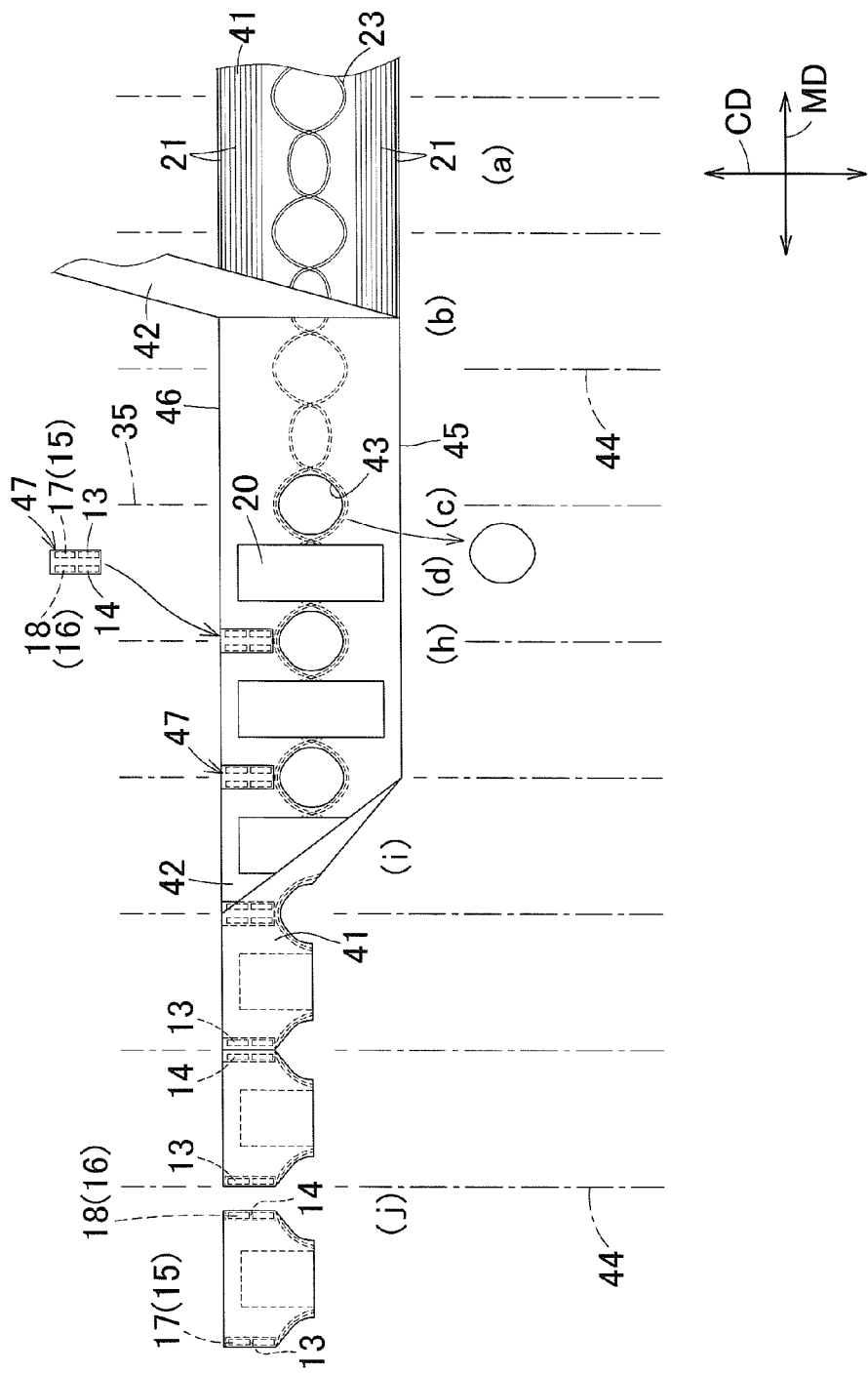
FIG. 3 is a schematic diagram illustrating a process of making the diaper.

Now a method of making such diaper 1 will be described. As schematically illustrated by FIG. 3, a continuous web comprising diapers 1 is formed in machine direction MD and finally severed along a cutting line 44 extending in a cross direction CD which is orthogonal to the machine direction MD to output the individual diapers 1. In the web comprising the diapers 1, the second lateral zones 12 and the first lateral zones 11 of the diapers 1 are respectively continuous one to another so that the transverse direction X of the diapers 1 coincides with the machine direction MD. In a first step (a), a first web 41 used to form the outer sheet 7 are fed and the waist elastic members 21 and the leg elastic members 23 are continuously attached to this first web 41 under tension in the machine direction MD. It should be appreciated that joining means such as adhesives used to attach these elastic members 21, 23 are not illustrated in FIG. 3.

In a second step (b), a second web 42 used to form the inner sheet 6 is fed toward and bonded to the first web 41. Both the first web 41 and the second web 42 are formed of fibrous webs. With respect to this second step (b) and later steps, the waist elastic members 21 are not illustrated and the leg elastic members 23 are indicated by dashed lines in the accompanying diagrams. In a third step (c), the first and second webs 41, 42 are formed with a circular opening 43 along a circle defined by the leg elastic members 23 so that peripheral edges of these opening 43 may define the peripheral edges 22 of the leg-openings 25. The cutting line 44 extends diametrically across the opening 43. In a fourth step (d), the liquid-absorbent core 20 is attached to the second web 42 by joining means (not shown) between each pair of the adjacent openings 43, 43 in the machines direction MD.

Figure 4:
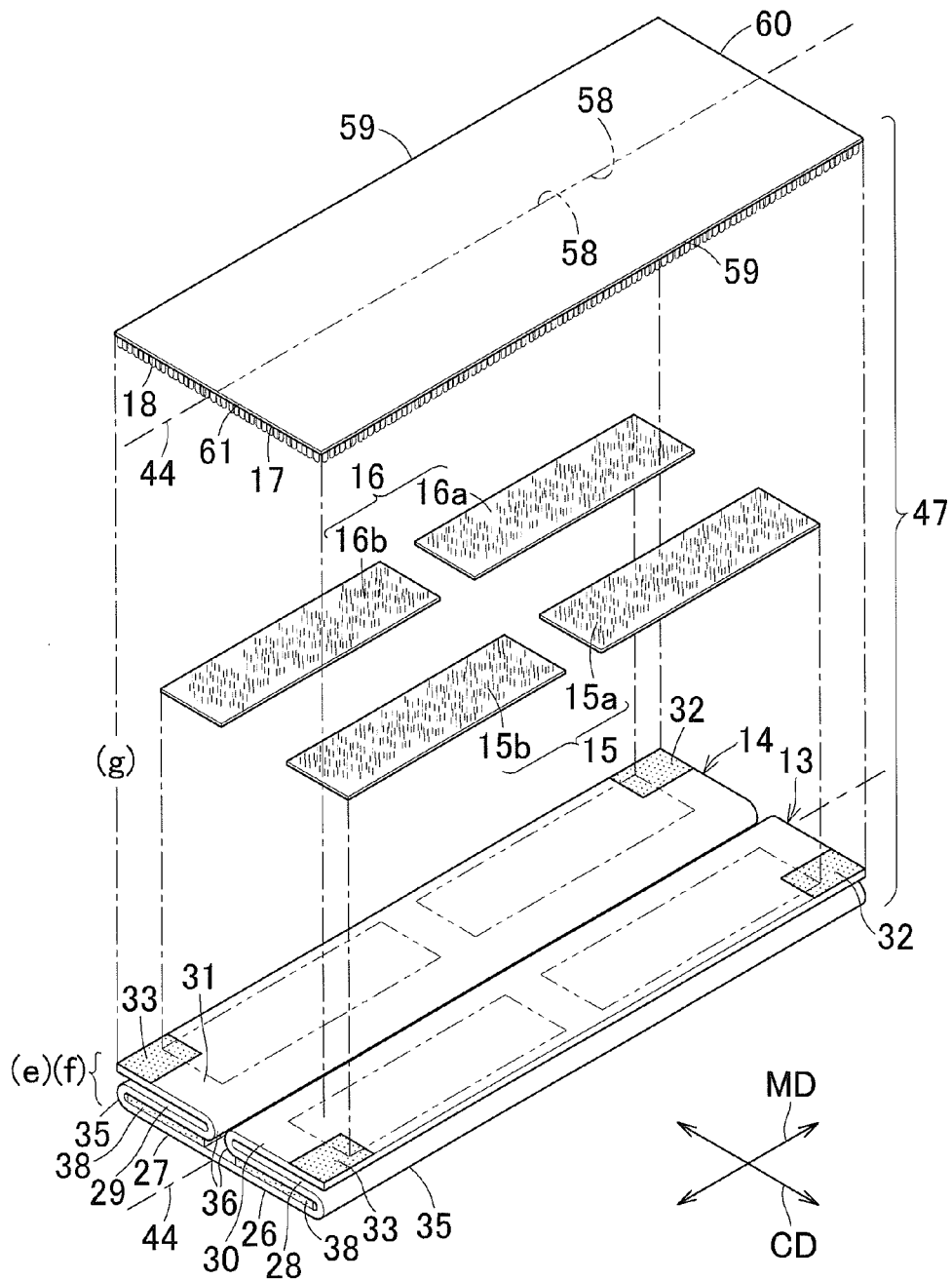
FIG. 4 is a schematic diagram partially illustrating the process of making the diaper.

FIG. 4 is a diagram schematically illustrating fifth to seventh steps (e), (f), (g) of forming a fastener assembly 47 comprising the mount members 13, 14, the hook elements 15, 16 and the loop elements 17, 18. In the fifth step (e), the mount members 13, 14 are folded back along first folding lines 35 and then along second folding line 36 so as to form first regions 26, 27, second regions 28, 29, and third regions 30, 31, respectively. The first regions 26, 27 extend from respective proximal ends of the mount members 13, 14 to the associated first folding lines 35, the second regions 28, 29 extend from the associated first folding lines 35 to the associated second folding lines 36, and the third regions 30, 31 extend from the associated second folding lines 36 to respective distal ends of the mount members 13, 14. The first regions 26, 27 are fixed to the associated second regions 28, 29 by adhesive layers 38. In the continuously made diapers, each set of the adjacent mount members 13, 14 may be formed of a single fibrous non-woven fabric attached to the second web 42 at once so that the first regions 26, 27 are contiguous to each other so as to extend in the cross direction CD. The first regions 26, 27 attached to the second web 42 are subsequently cut off along the cutting line 44. The mount members 13, 14 including these first regions 26, 27 are bilaterally symmetric about the cutting line 44, of which the mount member 13 presents an inverted Z-shape cross-section and the mount member 14 presents a Z-shaped cross-section.

In the fastener assembly 47, the mount members 13, 14 and the loop elements 17, 18 are length-dimensioned to be substantially the same in the machine direction MD as well as in the cross direction CD while the hook elements 15, 16 are length-dimensioned to be shorter than the loop elements 17, 18 in the machine direction MD as well as in the cross direction CD. In consequence, the loop elements 17, 18 are partially exposed outward beyond respective peripheral edges of the hook elements 15, 16 when the hook elements 15, 16 are engaged with the loop elements 17, 18. Each of the loop elements 17, 18 includes inner and outer lateral edges 58, 59 extending in the cross direction CD and upper and lower ends 60, 61 extending in the machine direction MD. The loop elements 17, 18 are subsequently cut off along the cutting line 44 to form inner lateral edge 58 on the cutting line 44.

Figure 5:
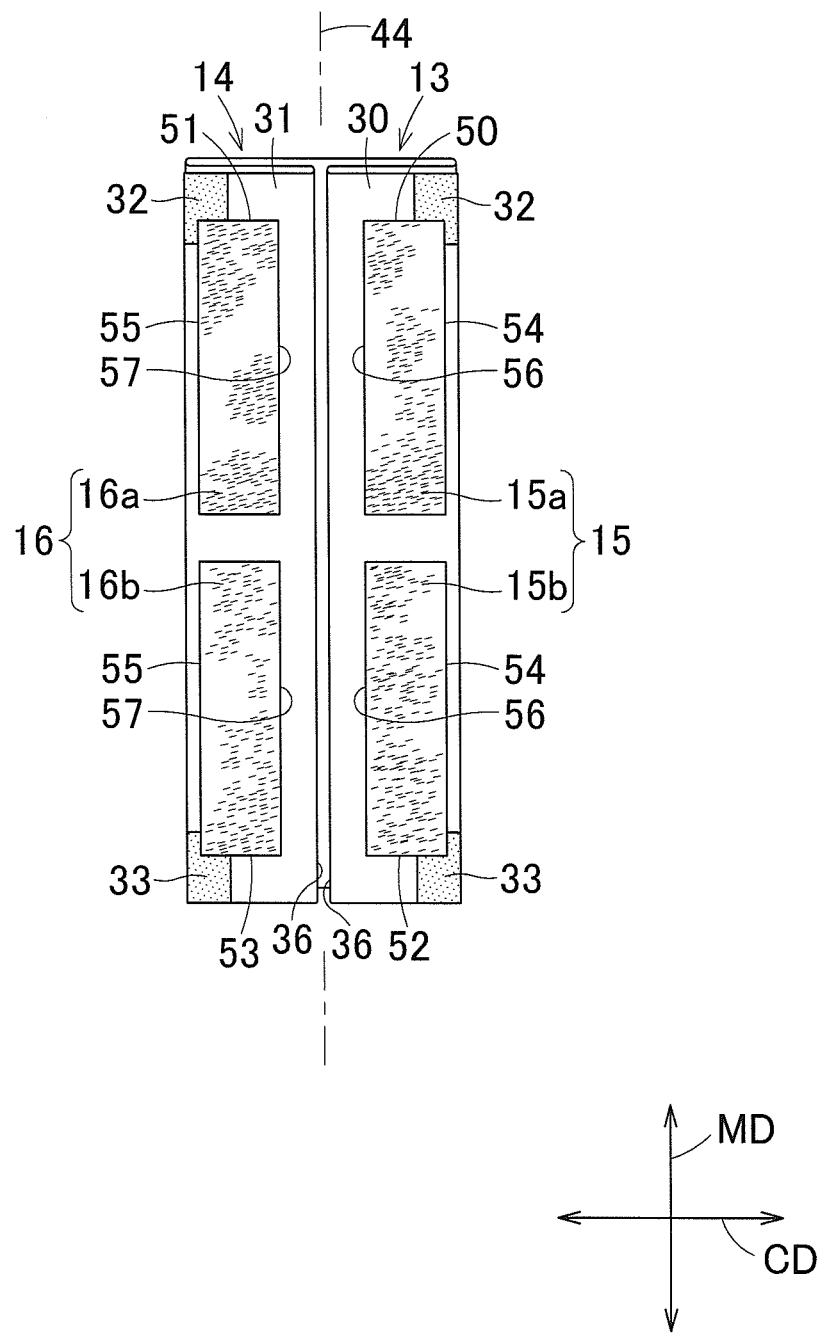
FIG. 5 is a schematic diagram illustrating sticking zones.

In the sixth step (f), the third regions 30, 31 of the respective mount members 13, 14 folded back on themselves are formed with sticking zones 32, 33 so that these sticking zones 32, 33 partially overlap the outer lateral edges 59 and the upper and lower ends 60, 61 of the respective loop elements 17, 18. Relative positions between the sticking zones 32, 33 and the hook elements 15, 16 are illustrated by FIG. 5. As illustrated, the third regions 30, 31 are provided with these sticking zones 32, 33 so as to face the upper and lower ends 60, 61 of the respective outer lateral edges 59 of the loop elements 17, 18 as viewed in the cross direction CD. The respective upper halves 15a, 16a of the hook elements 15, 16 include upper ends 50, 51 and the respective lower halves 15b, 16b include lower ends 52, 53. The respective hook elements 15, 16 further include lateral edges 54, 55 on one side and lateral edges 56, 57 on the other side. The sticking zones 32 respectively extend outward beyond the upper ends 50, 51 and the lateral edges 54, 55 on one side while the sticking zones 33 extend outward beyond the lower ends 52, 53 and the lateral edges 54, 55 on the other side.

In the seventh step (g), the hook elements 15, 16 are attached to the respective third regions 30, 31 of the mount members 13, 14. The hook elements 15, 16 may be previously engaged with the associated loop elements 17, 18 or the hook elements 15, 16 may be engaged with the associated loop elements 17, 18 after the hook elements 15, 16 have been attached to the associated third regions 30, 31. In both cases, the sticking zones 32, 33 provided on the mount members 13, 14 are temporarily joined to the associated loop elements 17, 18 by placing the hook elements 15, 16 into engagement with the associated loop elements 32, 33.

The sticking zones 32, 33 are provided between the third regions 30, 31 and the associated hook elements 15, 16 and therefore the sticking zones 32, 33 may sometimes be partially covered with the hook elements 15, 16. However, most part of the sticking zones 32, 33 extend outward beyond the hook elements 15, 16, i.e., exposed outside the associated hook elements 15, 16. The portions of the sticking zones 32, 33 exposed in this manner face the corners defined by the inner lateral edges 58 and the upper and lower ends 60, 61 of the loop elements 17, 18 and are temporarily joined to the mount members 13, 14 at the corners thereof.

In a eighth step (h), the fastener assembly 47 constructed as has been described above is fed toward the second web 42 as illustrated by FIG. 3. It should be understood that the fastener assembly 47 is turned by 90° in the course of being fed toward the second web 42. As a result, the machine direction MD as well as the cross direction CD indicated by the double-headed arrows in FIGS. 4 and 5 is inverted in FIG. 3. The first and second webs 41, 42 define one end 45 and the opposite end 46 both extending in the machine direction MD so that a section of the first and second webs 41, 42 extending aside toward the end 45 will define the front waist region 8 and a section thereof extending aside toward the opposite end 46 will define the rear waist region 9 of the diaper 1. The mount members 13, 14 are bonded to the portion of the second web 42 extending aside toward the opposite end 46 by adhesives (not shown).

In a ninth step (i), the web assembly comprising the first and second webs 41, 42 is folded in two with the opposite ends 45, 46 exactly placed upon each other and with the liquid-absorbent core 20 inside. The loop elements 17, 18 are bonded to the second web 42 at regions thereof placed aside toward the end 45 in the course of folding the web assembly comprising the first and second webs 41, 42 into two.

In a tenth step (j), the web assembly comprising the first and second webs 41, 42 folded in two is cut along the cutting line 44 to obtain the individual diaper 1 wherein the first lateral zones 11 of the front waist region 8 are defined by the end 45 of the web assembly comprising the first and second webs 41, 42 and the second lateral zones 12 of the rear waist region 9 are defined by the opposite end 46 of the web assembly. Thereupon, the mount members 13, 14 and the loop elements 17, 18 are also cut along the cutting line 44, respectively, so that the mount members 13, 14 extend along the first lateral zones 11 and the loop elements 17, 18 extend along the second lateral zones 12. The machine direction MD and the cross direction CD in the process of making the diaper 1 correspond to the transverse direction X and the longitudinal direction Y of the diaper 1, respectively.

According to the method of making the diaper 1 as has been described above, the third regions 30, 31 of the mount members 13, 14 are temporarily joined to the associated loop elements 17, 18 by the sticking zones 32, 33 so as to restrict the loop elements 17, 18 from riding up or curling up. While there is a tendency that the loop elements 17, 18, particularly the upper and lower ends thereof might be apt to ride up or curl up in the course of making the diaper 1, the sticking zones 32, 33 formed on the mount members 13, 14 at the upper and lower ends thereof enhance the restricting effect against such riding up or curling up of the loop elements 17, 18. In this way, the presence of the sticking zones 32, 33 serves to restrict the loop elements 17, 18 from riding up or curling up in the course of making the diaper 1 so as not to result in displacement of the web assembly and/or to slow down the production rate.

Adhesive strength of the sticking zones 32, 33 with respect to the loop elements 17, 18 is set to be lower than the engagement strength between the hook elements 15, 16 and the loop elements 17, 18. In consequence, when it is tried to disengage the hook elements 15, 16 from the loop elements 17, 18, temporary fixation of the loop elements 17, 18 by the sticking zones 32, 33 is easily released without making it difficult to disengage the hook elements 15, 16 from the loop elements 17, 18. The sticking zones 32, 33 have been described and illustrated to be provided on the third regions 30, 31 of the respective mount members 13, 14 so as to face corners defined by the outer lateral edges 59 and upper ends 60 and lower ends 61 of the respective loop elements 17, 18. However, the invention is not limited to such allocation of the sticking zones 32, 33 so far as it is possible to restrict the loop elements 17, 18 from riding up or curling up. For example, the sticking zones 32, 33 may be formed so as to face the upper and lower ends 60, 61, not intermittently but continuously over full length of these upper and lower ends 60, 61, respectively.

The sticking zones 32, 33 may be formed of materials having re-adherence properties. Use of such materials allows the sticking zones 32, 33 to be stuck again to the loop elements 17, 18 even after the temporary joint has been released. Consequentially, even when the hook elements 15, 16 are engaged again with the loop elements 17, 18 to put the diaper 1 on the wearer's body after the temporary joint by the sticking zones 32, 33 has been released and the hook elements 15, 16 have been disengaged from the loop elements 17, 18, it is possible for the sticking zones 32, 33 to restrict the loop elements 17, 18 from riding up or curling up with respect to the mount members 13, 14, respectively. By restricting the loop elements 17, 18 from riding up or curling up in the course of putting the diaper 1 on the wearer's body, it is also possible to restrict the area of engagement from being unacceptably reduced or uncomfortable feeling for the wearer from being generated or the loop elements 17, 18 from coming in direct contact with the wearer's skin and causing any type of skin trouble. In the case of a pants-type diaper used as the wearing article, the diaper can be put on the wearer's body without releasing the temporary joint and in, this case also, the presence of the sticking zones 32, 33 serve to restrict the hook elements 15, 16 from being unintentionally disengaged from the loop elements 17, 18 when the diaper is pulled up. It will be obviously understood that, in the case of such pants-type diaper also, the loop elements 17, 18 can be prevented from riding up or curling up.

While the hook elements 15, 16 are attached to the associated mount members 13, 14 and then the loop elements 17, 18 are attached to the hook elements 15, 16 to form the fastener assembly which is then attached to the second web 42 constituting the chassis 2 according to the embodiment as has been described, the invention is not limited to this embodiment. Alternatively, the hook elements 15, 16 may be attached to the second web 42 on its region put aside toward the end 46 thereof and the loop elements 17, 18 may be attached to the second web 42 on its region put aside toward the end 45 and thereafter the web assembly may be folded in two so as to engage the hook elements 15, 16 with the associated loop elements 17, 18. For the method of making the diaper 1 as has been described above, various timings for feeding of the liquid-absorbent core 20, forming of the opening 37 which define the peripheral edges of the respective leg-openings 25 and the other steps may be appropriately changed.

While the hook elements 15, 16 are attached to the front waist region 8 and the loop elements 17, 18 are attached to the rear waist region 9 according to the embodiment as has been described above, it is possible to reverse this relationship. Specifically, while the front waist region 8 has been designated as the first waist region and the rear waist region 9 has been designated as the second waist region, it is possible to designate the front waist region 8 as the second waist region and to designate the rear waist region 9 as the first waist region. In any case, it is desired to attach the hook elements to the second web 42 in a manner of which the hook elements having relatively high stiffness would not come in contact with the wearer's skin and cause any damage for the wearer's skin. While the diaper 1 includes the liquid-absorbent core 20 prepared separately of the chassis 2 according to the embodiment as has been described above, it is possible to sandwich the liquid-absorbent core between the inner and outer sheets 6, 7 of the chassis 2.

While each of the mount members 13, 14 are folded along the first and second folding lines in three to define the first, second and third regions so as to present the substantially Z-shaped or inverted Z-shaped cross-section according to the embodiment as has been described and illustrated, the invention is not limited to such embodiment. For example, the each of the mount members 13, 14 may be folded in two toward the longitudinal center line P-P so as to define the second and third regions. The sticking zones 32, 33 may be formed of commonly used materials in the relevant technical field such as adhesives, thermal- or ultrasonic bonds. While these sticking zones 32, 33 are formed between the loop elements 17, 18 and the mount members 13, 14 to temporarily join the loop elements 17, 18 to the mount members 13, 14 according to the embodiment as has been described and illustrated, it is also possible to form the sticking zones 32, 33 between the loop elements 17, 18 and the hook elements 15, 16. In any case, it is important to restrict the temporary joint between the loop elements 17, 18 and the mount members 13, 14 from affecting the engagement between the loop elements 17, 18 and the hook elements 15, 16.

The invention claimed is:

1. A method of making a wearing article having a chassis and a fastener assembly, said chassis having a longitudinal direction, a transverse direction, a side facing a wearer's skin and a side facing a wearer's garment, a first waist region corresponding to one of front and rear waist regions, a second waist region corresponding to the other of said front and rear waist regions and a crotch region extending between said first and second waist regions and said fastener assembly including first fastening regions provided along a pair of first lateral zones of said first waist region opposed to each other in said transverse direction and extending in said longitudinal direction and second fastening regions provided along a pair of second lateral zones of said second waist region opposed to each other in said transverse direction and extending in said longitudinal direction wherein said first fastening regions are detachably engaged with said second fastening regions and wherein said first fastening regions include hook elements and said second fastening regions include loop elements, wherein each of said second fastening regions includes inner and outer side edges extending in said longitudinal direction and upper and lower ends extending in said transverse direction,
wherein a process of making said wearing article includes a machine direction (MD) and a cross direction (CD) orthogonal to said machine direction and, in a course of continuously making said chassis, said transverse direction of said chassis is aligned in said machine direction,
said method of making the wearing article comprising the steps of:
forming said fastener assembly,
feeding a web assembly forming said chassis in said machine direction, and
bonding said fastener assembly to said web assembly, said step of forming said fastener assembly further comprising the steps of:
forming said first fastening regions with sticking zones adapted to be temporarily joined to said second fastening regions;
attaching said hook elements to said first fastening regions to partially cover said sticking zones by said hook elements,
said sticking zones being formed so as to face and be aligned with corners defined by said outer side edges and upper and lower ends of said second fastening regions in engagement with said first fastening regions,
said sticking zones formed separately and discretely in four corners of said first fastening regions and having an adhesive strength with respect to contact with said loop elements that is lower than an engagement strength between said hook elements and said loop elements, and
bringing said hook elements of said first fastening regions into engagement with said loop elements of said second fastening regions and at the same time temporarily joining said first fastening regions to said second fastening regions by parts of said sticking zones that extend outward beyond the hook elements to form said fastener assembly.

2. The method of making the wearing article defined by claim 1, said method of making the wearing article further includes the steps of:
cutting said web assembly in said cross direction after bonding said fastener assembly to said web assembly.

3. The method of making the wearing article defined by claim 1, wherein said first fastening regions include mount members extending outward beyond said first lateral zones by intermediary of which said hook elements are attached to said first lateral zones.

4. The method of making the wearing article defined by claim 3 wherein said sticking zones temporarily join said mount members to said loop elements.

5. The method of making the wearing article defined by claim 4, wherein said loop elements occupy an area larger than an area occupied by said hook elements and said loop elements exposed outside said hook elements are temporarily joined to said mount members by said sticking zones.

6. The method of making the wearing article defined by claim 2, wherein each of said second fastening regions includes inner and outer side edges extending in said longitudinal direction and upper and lower ends extending in said transverse direction and said sticking zones are formed so as to face corners defined by said outer side edge and upper and lower ends of said second fastening regions in engagement with said first fastening regions.

7. The method of making the wearing article defined by claim 2, wherein said first fastening regions include mount members extending outward beyond said first lateral zones by intermediary of which said hook elements are attached to said first lateral zones.

8. The method of making the wearing article defined by claim 1, wherein said first fastening regions include mount members extending outward beyond said first lateral zones by intermediary of which said hook elements are attached to said first lateral zones.

9. The method of making the wearing article defined by claim 6, wherein said first fastening regions include mount members extending outward beyond said first lateral zones by intermediary of which said hook elements are attached to said first lateral zones.

10. The method of making the wearing article defined by claim 7 wherein said sticking zones temporarily join said mount members to said loop elements.

11. The method of making the wearing article defined by claim 8 wherein said sticking zones temporarily join said mount members to said loop elements.

12. The method of making the wearing article defined by claim 9 wherein said sticking zones temporarily join said mount members to said loop elements.

13. The method of making the wearing article defined by claim 10, wherein said loop elements occupy an area larger than an area occupied by said hook elements and said loop elements exposed outside said hook elements are temporarily joined to said mount members by said sticking zones.

14. The method of making the wearing article defined by claim 11, wherein said loop elements occupy an area larger than an area occupied by said hook elements and said loop elements exposed outside said hook elements are temporarily joined to said mount members by said sticking zones.

15. The method of making the wearing article defined by claim 12, wherein said loop elements occupy an area larger than an area occupied by said hook elements and said loop elements exposed outside said hook elements are temporarily joined to said mount members by said sticking zones.

* * * * *